US010844033B2

(12) United States Patent
Dastgir et al.

(10) Patent No.: US 10,844,033 B2
(45) Date of Patent: Nov. 24, 2020

(54) METHOD FOR PREPARING DELTA-LACTONES

(71) Applicants: Qatar Foundation For Education, Science and Community Development, Doha (QA); Sultan Qaboos University, Muscat (OM); Leibniz-Institut Fur Katalyse e.V. an der Universitat Rostock, Rostock (DE)

(72) Inventors: Sarim Dastgir, Doha (QA); Badria Al-Shihi, Muscat (OM); Mohammad Sharif, Rostock (DE); Matthias Beller, Rostock (DE); Ralf Jackstell, Rostock (DE)

(73) Assignees: Qatar Found. For Ed., Science and Community Development, Doha (QA); Sultan Qaboos University, Muscat (OM); Leibniz-Institut Fur Katalyse e.V. an der Unversitat Rostock, Rostock (DE)

( * ) Notice: Subject to any disclaimer, the term of this patent is extended or adjusted under 35 U.S.C. 154(b) by 23 days.

(21) Appl. No.: 16/095,512

(22) PCT Filed: May 16, 2017

(86) PCT No.: PCT/EP2017/061691
§ 371 (c)(1),
(2) Date: Oct. 22, 2018

(87) PCT Pub. No.: WO2017/202644
PCT Pub. Date: Nov. 30, 2017

(65) Prior Publication Data
US 2019/0127343 A1     May 2, 2019

(30) Foreign Application Priority Data

May 26, 2016    (GB) .................................. 1609314.8

(51) Int. Cl.
    *C07D 309/30*     (2006.01)
    *C07D 309/32*     (2006.01)

(52) U.S. Cl.
    CPC ................................. *C07D 309/32* (2013.01)

(58) Field of Classification Search
    CPC ............................ C07D 309/32; C07D 309/30
    USPC ........................................................ 549/273
    See application file for complete search history.

(56) References Cited

FOREIGN PATENT DOCUMENTS

| EP | 0 050 445 A1 | 4/1982 |
|---|---|---|
| EP | 0 124 725 A1 | 11/1984 |
| GB | 2 003 875 A | 3/1979 |

OTHER PUBLICATIONS

Yao Dai et al: "Preparation and application of air-stable, P,N-bidentate ligands for the selective synthesis of delta-lactone via the palladium-catalyzed telomerization of 1,3-butadiene with carbon dioxide", Journal of Organometallic Chemistry, Elsevier-Sequoia S.A. Lausanne, CH, vol. 696, No. 26, Oct. 6, 2011 (Oct. 6, 2011), pp. 4309-4314.

Arno Behr et al: "Telomerisation von Kohlendioxid und 1,3-Butadien: Verfahrensentwicklung via Miniplant-Technik", Chemie Ingenieur Technik., vol. 72, No. 1-2, Jan. 1, 2000 (Jan. 1, 2000), pp. 58-61, Weinheim, DE.

Arno Behr et al: "The telomerisation of 1,3-butadiene and carbon dioxide: process development and optimisation in a continuous miniplant", Dalton Transactions: The International Journal for Inorganic, Organometallic and Bioinorganic Chemistry, No. 38, Jan. 1, 2006 (Jan. 1, 2006), pp. 4607-4613.

A. Behr et al: "Palladium-katalysierte Telomerisation von Kohlendioxid mit Butadien im Labor- und Miniplantmaßstab", Chemie Ingenieur Technik., vol. 76, No. 12, Dec. 17, 2004 (Dec. 17, 2004), pp. 1828-1832, Weinheim, DE.

Klaus Buchmuller et al: "Control of homogeneously catalyzed reactions by phase equilibria. This work was presented at the Green Solvents for Catalysis Meeting held in Bruchsal, Germany, Oct. 13-16, 2000.", Green Chemistry, vol. 5, No. 2, Apr. 8, 2003 (Apr. 8, 2003), pp. 218-223.

Arno Behr et al: "Aqueous biphasic catalysis as a powerful tool for catalyst recycling in telomerization and hydrogenation chemistry. This work was presented at the Green Solvents for Catalysis Meeting held in Bruchsal, Germany Oct. 13-16, 2002.", Green Chemistry, vol. 5, No. 2, Apr. 8, 2003 (Apr. 8, 2003), pp. 198-204.

Behr A et al: "Selective catalytic formation of unsaturated amino acids from petrochemicals and carbon dioxide-Application of high-throughput catalyst screening", Journal of Molecular Catalysis A: Chemical, Elsevier, Amsterdam, NL, vol. 287, No. 1-2, May 15, 2008 (May 15, 2008), pp. 95-101.

Behr A et al: "Homogeneous and heterogeneous catalyzed three-step synthesis of 2-ethylheptanoic acid from carbon dioxide, butadiene and hydrogen", Journal of Molecular Catalysis A: Chemical, Elsevier, Amsterdam, NL, vol. 187, No. 1, Jan. 1, 2002 (Jan. 1, 2002), pp. 69-80.

A. Musco et al: "Telomerization Reactions of Butadiene and CO2 Catalyzed by Phosphine Pd(0) Complexes: (E)-2-Ethylidenehept-6-en-5-olide and Octadienyl Esters of 2-Ethylidenehepta-4,6-dienoic Acid", Inorganica Chimica Acta, vol. 28, Jan. 1, 1978 (Jan. 1, 1978), pp. 147-148, Milan, Italy.

Arno Behr et al: "Telomerization of Carbon Dioxide and 1,3-Butadiene: Process Development in a Miniplant", Chemical Engineering and Technology, vol. 23, No. 11, 2000, pp. 952-955.

(Continued)

*Primary Examiner* — Charanjit Aulakh
(74) *Attorney, Agent, or Firm* — Hoffmann & Baron, LLP (57) ABSTRACT

The present invention relates to methods of forming delta-lactone compounds by reaction of a diene with carbon dioxide in the presence of Pd and a phosphine ligand.

12 Claims, 3 Drawing Sheets

(56) References Cited

OTHER PUBLICATIONS

Dinjus, E. et al, "New insights into the Palladium-Catalysed Synthesis of delta-Lactones from 1,3-Dienes and Carbon Dioxide", Applied Organometallic Chemistry, vol. 9, No. 1, 1995, pp. 43-50.
Behr, A. et al, "Possibilities of Controlling Transition Metal-catalysed Reactions of 1,3-Dienes with Carbon Dioxide", Chemische Berichte, vol. 119, No. 3, 1986, pp. 991-1015.
Behr, A. et al, "Synthese von 2-Ethyliden-g-hepten-5-olid", Synthesis, vol. 1983, No. 7, 1983, p. 574.
International Search Report, International Application No. PCT/EP2017/061691, dated Sep. 6, 2017.
Written Opinion of the International Searching Authority, International Application No. PCT/EP2017/061691, dated Sep. 6, 2017.
UK Search Report, Application No. GB1609314.8, dated Mar. 8, 2017.

METHOD FOR PREPARING DELTA-LACTONES

This application is a U.S. National Stage filing under 35 U.S.C. § 371 of International Application No. PCT/EP2017/061691, filed May 16, 2017, which in turn claims priority to British Patent Application No. 1609314.8, filed May 26, 2016, the entire contents of which are incorporated by reference herein in their entirety.

The present invention relates to methods of forming compounds. In particular, the present invention relates to methods of telomerizing dienes.

BACKGROUND

Fossil fuels are a diminishing and finite resource. Fossil fuels are processed to form fine and bulk chemicals for a multiplicity of uses.

There is a continuing need for sustainable approaches to the synthesis of fine and bulk chemicals using readily available raw materials as alternatives to using fossil fuels.

So called "green chemistry" considers in some aspects possible ways of using carbon dioxide to form fine and bulk chemicals. Carbon dioxide is a biological by-product as well as an industrial waste material, including from the burning of fossil fuels. Indeed, an increase in atmospheric carbon dioxide levels is believed to result in global warming. Therefore, the use of carbon dioxide in producing fine and bulk chemicals is a desirable goal.

Organic synthesis can be directed to the development of chemical reactions with high atom efficiency. Carbon dioxide gas, and carbon dioxide in its bound form as carbonates, is a plentiful C1 source which can be utilised to form chemical precursors to fine and bulk chemicals.

There are limited reports on the potential use of carbon dioxide in organic syntheses; the examples include the industrial synthesis of nitrogen fertilisers (urea), organic carbonates and polycarbonates, and their subsequent applications for various processes.

The reaction of 1,3 butadiene with carbon dioxide to form δ-lactone (1) has been studied. δ-lactone (1) can be used as a precursor to a wide variety of fine and bulk chemicals.

The palladium-catalyzed telomerization of 1,3-butadiene with carbon dioxide has been studied. This transformation results in the valorization of carbon dioxide as a building block for organic syntheses.

The work of Inoue et al. and Musco et al. in the 1970s followed by the work of Behr et al. in the early 1980s was directed to the synthesis of δ-lactone (1) by the chemical fixation of carbon dioxide into 1,3-butadiene. Several other telomerized products, e.g synthesis of acids, esters, amines and 5-membered lactones have been the subject of studies also, using carbon dioxide as a feedstock.

The Pd-catalyzed telomerization of 1,3-butadiene with $CO_2$ is an example of the catalytic formation of a new C—C bond between $CO_2$ and an organic compound. Hence, this telomerization process is a means of using $CO_2$ as a C1-building block in synthetic organic chemistry (Scheme 1).

Scheme 1

A. Behr's work
Yield of 1 35% isolated

K. Nozaki's work
Yield of 1 20% isolated

The generally accepted mechanism for the formation of δ-lactone (1) (Scheme 2) includes 1,3-butadiene telomerization with carbon dioxide in the presence of a phosphine ligand. In the generally accepted mechanism, two 1,3-butadiene molecules are added to the palladium (0) phosphine complex generated from palladium (II) and phosphines in situ, forming the $\eta^3$-allyl complex (5), which is in equilibrium with (6) and either reacts with (6a) or to the complex (7).

Scheme 2. Generally accepted mechanism for δ-lactone 1

The complex (7) is formed in the following step by insertion of carbon dioxide to (6) which on ring closure gives products (1) and (2) and several others by products like (4), (4a) have also been observed.

Previously described Pd-catalyzed telomerizations of 1,3-butadiene generally give low yields and low product selectivities.

The present invention seeks to address the problems identified above.

SUMMARY

According to a first aspect of the present invention, there is provided a method of forming a compound of formula (I):

(I)

the method comprising the steps of:
(i) providing a compound of the formula (II), (III) or (IV):

(II)

(III)

(IV)

wherein,
$R_1$ is H, unsubstituted alkyl, substituted alkyl, unsubstituted phenyl or substituted phenyl;
$R_2$ is H, unsubstituted alkyl, substituted alkyl, unsubstituted phenyl or substituted phenyl;
$R_3$ is H;
$R_4$ is H, unsubstituted alkyl, substituted alkyl, unsubstituted phenyl or substituted phenyl; and, (ii) reacting the compound of formula (II), (III) or (IV) with $CO_2$ in the presence of a source of Pd(0) and a phosphine ligand to form a compound of formula (I).

Preferably, wherein the phosphine ligand is of the formula (PI):

$$PR_5R_6R_7 \qquad (PI),$$

wherein:
- $R_5$ is substituted aryl, unsubstituted aryl, substituted linear alkyl, unsubstituted linear alkyl, substituted cyclic alkyl, unsubstituted cyclic alkyl, substituted cyclic heteroalkyl, unsubstituted cyclic heteroalkyl, unsubstituted adamantyl or substituted adamantyl;
- $R_6$ is substituted aryl, unsubstituted aryl, substituted linear alkyl, unsubstituted linear alkyl, substituted cyclic alkyl, unsubstituted cyclic alkyl, substituted cyclic heteroalkyl, unsubstituted cyclic heteroalkyl, unsubstituted adamantyl or substituted adamantyl; and,
- $R_7$ is substituted aryl, unsubstituted aryl, substituted linear alkyl, unsubstituted linear alkyl, substituted cyclic alkyl, unsubstituted cyclic alkyl, substituted cyclic heteroalkyl, unsubstituted cyclic heteroalkyl, unsubstituted adamantyl or substituted adamantyl.

Further preferably, wherein substituted aryl or unsubstituted aryl refers to aromatic hydrocarbons with a conjugated cyclic molecular ring structure of 3, 4, 5, 6, 7, 8, 9, 10, 11 or 12 carbon atoms; optionally, aryl refers to monocyclic, bicyclic or polycyclic rings.

Advantageously, wherein substituted linear alkyl or unsubstituted linear alkyl refers to straight-chain or branched-chain hydrocarbons having 1, 2, 3, 4, 5, 6, 7, 8, 9, 10, 11, 12, 13, 14, 15, 16, 17, 18, 19 or 20 carbon atoms linked exclusively by single bonds.

Preferably, wherein substituted cyclic alkyl or unsubstituted cyclic alkyl refers to cyclic hydrocarbons having 3, 4, 5, 6, 7, 8, 9, 10, 11, 12, 13, 14, 15, 16, 17, 18, 19 or 20 carbon atoms linked exclusively by single bonds.

Further preferably, wherein substituted cyclic heteroalkyl or unsubstituted cyclic heteroalkyl refers to cyclic hydrocarbons having 3, 4, 5, 6, 7, 8, 9, 10, 11, 12, 13, 14, 15, 16, 17, 18, 19 or 20 carbon atoms and any one of 1, 2, 3, 4, 5, 6, 7 or 8 heteroatoms in the cyclic structure.

Advantageously, wherein the heteroatoms are independently N, S, O or P.

Preferably, wherein at least one of $R_5$, $R_6$ and $R_7$ is substituted aryl.

Further preferably, wherein substituted aryl or unsubstituted aryl is substituted phenyl or unsubstituted phenyl.

Advantageously, wherein the term substituted refers to the particular moiety substituted with 1, 2, 3, 4, 5, 6, 7, 8, 9, 10, 11, 12, 13, 14, 15, 16, 17, 18, 19 or 20 substituents selected from the group consisting of H, alkyl, aryl, alkenyl, alkynyl, arylalkyl, alkoxy, aryloxy, arylalkoxy, alkoxyalkylaryl, alkylamino, arylamino, 2-OMe-Ph, phenyl, 2-furyl, $NH_2$, OH, CN, $NO_2$, $OCF_3$, $CF_3$, Br, Cl, F, 1-amidino, 2-amidino, alkylcarbonyl, morpholino, piperidinyl, dioxanyl, pyranyl, heteroaryl, furanyl, thiophenyl, tetrazolo, thiazole, isothiazolo, imidazolo, thiadiazole, thiadiazole S-oxide, thiadiazole S,S-dioxide, pyrazolo, oxazole, isoxazole, pyridinyl, pyrimidinyl, quinoline, isoquinoline, SR''', SOR''', $SO_2R'''$, $CO_2R'''$, COR''', CONR'''R''', CSNR'''R''' and $SO_nNR'''R'''$, wherein R''' is alkyl or substituted alkyl.

Preferably, wherein $R_5$, $R_6$ and $R_7$ are the same; or, $R_5$ and $R_6$ are the same and $R_7$ is different; or, $R_6$ and $R_7$ are the same and $R_5$ is different; or, $R_5$ and $R_7$ are the same and $R_6$ is different.

Further preferably, wherein the phosphine ligand is not tricyclohexylphosphine ($PCy_3$).

Advantageously, wherein the phosphine ligand is any one of:

$P(2\text{-}OMe\text{-}Ph)_3$, $PPh_3$, $P(2\text{-}furyl)_3$, wherein Ph is —C$_6$H$_5$, Cy is —C$_6$H$_{11}$, Me is —CH$_3$ and Ad is adamantyl.

Preferably, wherein the source of Pd(0) is any one of Pd(acac)$_2$, Pd(OAc)$_2$, PdCl$_2$(MeCN)$_2$, Pd(dba)$_2$, [PdCl(allyl)]$_2$ or Pd$_2$(dba)$_3$; or, a Pd(II) complex that can be reduced in situ to produce Pd(0) species.

Further preferably, wherein R$_1$, R$_2$, R$_3$ and R$_4$ are each H.

Advantageously, wherein the step of providing a compound of formula (I) includes providing 1,3-butadiene Preferably, wherein the method is a method of forming δ-lactone, namely, Further preferably, wherein the step of reacting the compound of formula (II), (III) or (IV) with CO$_2$ in the presence of a source of Pd(0) and a phosphine ligand to form a compound of formula (I) takes place in a solvent.

Advantageously, wherein the solvent is MeCN, propylene carbonate or ethylene carbonate.

Preferably, wherein the step of reacting the compound of formula (II), (III) or (IV) with CO$_2$ in the presence of a source of Pd(0) and a phosphine ligand to form a compound of formula (I) utilises CO$_2$ as a reactant in gaseous form.

Further preferably, wherein the method is a method of forming δ-lactone, namely,
the method comprising the steps of:
(i) providing 1,3-butadiene and,
(ii) reacting 1,3-butadiene with CO$_2$ in the presence of a source of Pd(0) and a phosphine ligand to form δ-lactone.

Advantageously, wherein the source of Pd(0) is Pd(acac)$_2$.

Preferably, wherein the phosphine ligand is P(2-OMe-Ph)$_3$ (TOMP; tris(2-methoxyphenyl)phosphine).

In another aspect of the present invention, there is provided a compound of formula (I) obtained by a method according to any of the methods above.

In another aspect of the present invention, there is provided a compound of formula (I) obtainable by a method according to any of the methods above.

In another aspect of the present invention, there is provided a method of forming an acid, an ester, an alcohol, a diol, an aldehyde, an amine, a bicyclic acid, a bicyclic aster, a tricyclic ester; the method comprising the step of:
(i) functionalising a compound of formula (I).

Preferably, wherein the step of functionalising a compound of formula (I) is any one of the following transformations:

The presently claimed invention demonstrates that carbon dioxide can be combined with organic moieties bearing double bonds, for example 1,3-butadiene, in the presence of Pd(0) and a phosphine, to form commercially useful organic compounds.

BRIEF DESCRIPTION OF THE DRAWINGS

Embodiments of the invention are described below with reference to the accompanying drawings, in which.

DETAILED DESCRIPTION

The following explanations of terms and methods are provided to better describe the present compounds and methods, and to guide those of ordinary skill in the art in the practice of the present disclosure. It is also to be understood that the terminology used in the disclosure is for the purpose of describing particular embodiments and examples only and is not intended to be limiting.

"Aryl" refers to substituted or unsubstituted aromatic hydrocarbons with a conjugated cyclic molecular ring structure of 3, 4, 5, 6, 7, 8, 9, 10, 11 or 12 carbon atoms. Optionally, aryl includes monocyclic, bicyclic or polycyclic rings. Optionally, aryl includes 1, 2 or 3 additional ring structures selected from the group consisting of a cycloalkyl, a cycloalkenyl, a heterocycloalkyl, a heterocycloalkenyl, or a heteroaryl. Optionally, aryl includes phenyl (benzenyl), thiophenyl, indolyl, naphthyl, totyl, xylyl, anthracenyl, phenanthryl, azulenyl, biphenyl, naphthalenyl, 1-methylnaphthalenyl, acenaphthenyl, acenaphthylenyl, anthracenyl, fluorenyl, phenalenyl, phenanthrenyl, benzo[a]anthracenyl, benzo[c]phenanthrenyl, chrysenyl, fluoranthenyl, pyrenyl, tetracenyl (naphthoacenyl), triphenylenyl, anthanthrenyl, benzopyrenyl, benzo[a]pyrenyl, benzo[e]fluoranthenyl, benzo[ghi]perylenyl, benzo[j]fluoranthenyl, benzo[k]fluoranthenyl, corannulenyl, coronenyl, dicoronylenyl, helicenyl, heptacenyl, hexacenyl, ovalenyl, pentacenyl, picenyl, perylenyl, and tetraphenylenyl. Optionally, aryl refers to aryls substituted with 1, 2, 3, 4 or 5 substituents selected from the group consisting of H, alkyl, aryl, alkenyl, alkynyl, arylalkyl, alkoxy, aryloxy, arylalkoxy, alkoxyalkylaryl, alkylamino, arylamino, 2-OMe-Ph, $NH_2$, OH, CN, $NO_2$, $OCF_3$, $CF_3$, Br, Cl, F, 1-amidino, 2-amidino, alkylcarbonyl, morpholino, piperidinyl, dioxanyl, pyranyl, heteroaryl, furanyl, thiophenyl, tetrazolo, thiazole, isothiazolo, imidazolo, thiadiazole, thiadiazole S-oxide, thiadiazole S,S-dioxide, pyrazolo, oxazole, isoxazole, pyridinyl, pyrimidinyl, quinoline, isoquinoline, SR''', SOR''', $SO_2R'''$, $CO_2R'''$, COR''', CONR'''R''', CSNR'''R''' and $SO_nNR'''R'''$, wherein R''' is alkyl or substituted alkyl.

"Cyclic Alkyl" refers to substituted or unsubstituted cyclic hydrocarbons having 3, 4, 5, 6, 7, 8, 9, 10, 11, 12, 13, 14, 15, 16, 17, 18, 19 or 20 carbon atoms linked exclusively by single bonds. Optionally, cyclic alkyl includes cyclopropane, cyclobutane, cyclopentane, cyclohexane, cycloheptane or cyclooctane.

"Linear Alkyl" refers to substituted or unsubstituted straight-chain or branched-chain hydrocarbons having 1, 2, 3, 4, 5, 6, 7, 8, 9, 10, 11, 12, 13, 14, 15, 16, 17, 18, 19 or 20 carbon atoms linked exclusively by single bonds and not having any cyclic structure. Optionally, linear alkyl includes methyl, ethyl, n-propyl, isopropyl, n-butyl, isobutyl, sec-butyl, tert-butyl, pentyl, iso-amyl, hexyl, heptyl, octyl, noyl, decyl, undecyl, dodecyl tridecyl, tetradecyl, pentadecyl, hexadecyl, heptadecyl, octadecyl, nonadecyl and eicosyl.

"Nucleophile" refers to a chemical species that donates an electron pair to an electrophile to form a chemical bond.

"Optional" or "optionally" means that the subsequently described event or circumstance can but need not occur, and that the description includes instances where said event or circumstance occurs and instances where it does not.

"Phenyl" refers to a cyclic group of atoms with the formula —$C_6H_5$. "Substituted phenyl" refers to a phenyl group where 1, 2, 3, 4, or 5 of the H atoms are substituted.

"Phosphine" refers to organophosphorous compounds of the formula $PR_5R_6R_7$ (PI).

"Source of Pd(0)" refers to organopalladium compounds where palladium is present in the zero oxidation state or in the +2 oxidation state. Non-limiting examples of sources of Pd(0) include $Pd(acac)_2$, $Pd(OAc)_2$, $PdCl_2(MeCN)_2$, $Pd(dba)_2$, $[PdCl(allyl)]_2$ or $Pd_2(dba)_3$. Alternatively, sources of Pd(0) include Pd(II) complexes that can be reduced in situ to produce Pd(0) species.

"Substituted" refers to the particular moiety substituted with 1, 2, 3, 4, 5, 6, 7, 8, 9, 10, 11, 12, 13, 14, 15, 16, 17, 18, 19 or 20 substituents selected from the group consisting of H, alkyl, aryl, alkenyl, alkynyl, arylalkyl, alkoxy, aryloxy, arylalkoxy, alkoxyalkylaryl, alkylamino, arylamino, 2-OMe-Ph, phenyl, 2-furyl, $NH_2$, OH, CN, $NO_2$, $OCF_3$, $CF_3$, Br, Cl, F, 1-amidino, 2-amidino, alkylcarbonyl, morpholino, piperidinyl, dioxanyl, pyranyl, heteroaryl, furanyl, thiophenyl, tetrazolo, thiazole, isothiazolo, imidazolo, thiadiazole, thiadiazole S-oxide, thiadiazole S,S-dioxide, pyrazolo, oxazole, isoxazole, pyridinyl, pyrimidinyl, quinoline, isoquinoline, SR''', SOR''', $SO_2R'''$, $CO_2R'''$, COR''', CONR'''R''', CSNR'''R''' and $SO_nNR'''R'''$, wherein R''' is alkyl or substituted alkyl.

"Telomerization" or "telomerizing" refers to the linear addition of dienes with the simultaneous addition of a nucleophile in a catalytic reaction. In one non-limiting example, "telomerization" or "telomerizing" refers to the dimerization of 1,3-dienes.

"TON" refers to turnover number. Turnover number is the number of moles of substrate that a mole of catalyst can convert before becoming inactivated.

"Unsubstituted" refers to the particular moiety without any substituents.

EXAMPLES

General Considerations

All reactions were carried out using standard Schlenk techniques under argon. δ-lactone (1) synthesis and was performed in a 160 mL or 50 mL stainless autoclave from Parr Instruments.

Reagents and Materials

Acetonitrile (MeCN) was dried by refluxing with $CaH_2$ and was distilled under argon (Ar) before use or purchased from Sigma-Aldrich.

$PdCl_2(MeCN)_2$, $Pd(acac)_2$, $Pd(OAc)_2$, Tris(dibenzylideneacetone) dipalladium ($Pd_2(dba)_3$), Tricyclohexylphosphine ($PCy_3$), phenylphosphine ($PPh_3$) and other Palladium precursors and phosphine ligands mentioned in the manuscript were purchased from the Sigma-Aldrich. 1,3-Butadiene, 1,2-Butadiene and $CO_2$ were purchased from the Evonik Industries.

Characterization

Figure 1:
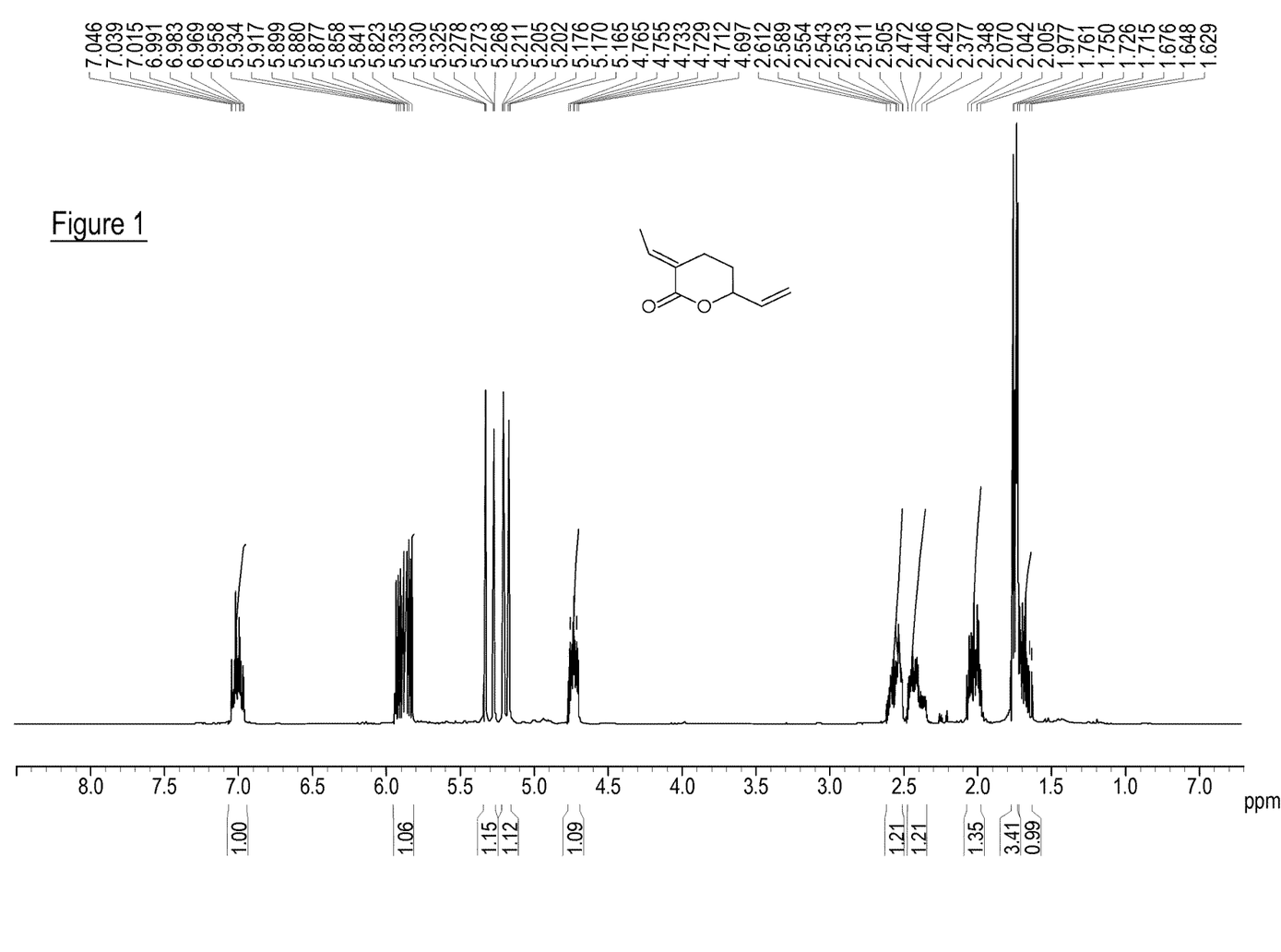
FIG. 1 shows a $^1$H NMR spectrum for δ-lactone (1) formed according to a method of the present invention.
Figure 2:
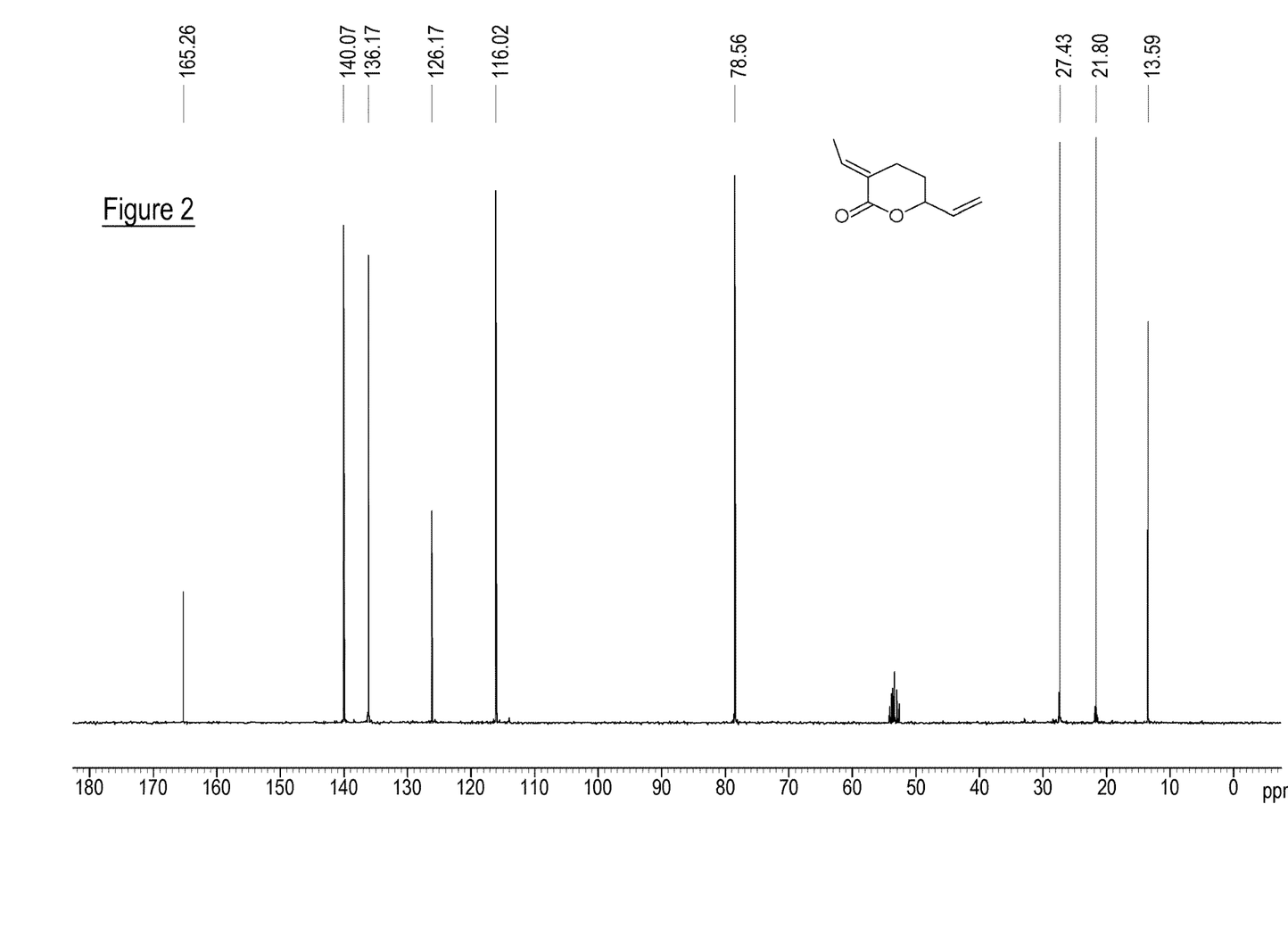
FIG. 2 shows a $^{13}$C NMR spectrum for δ-lactone (1) formed according to a method of the present invention.
Figure 3:
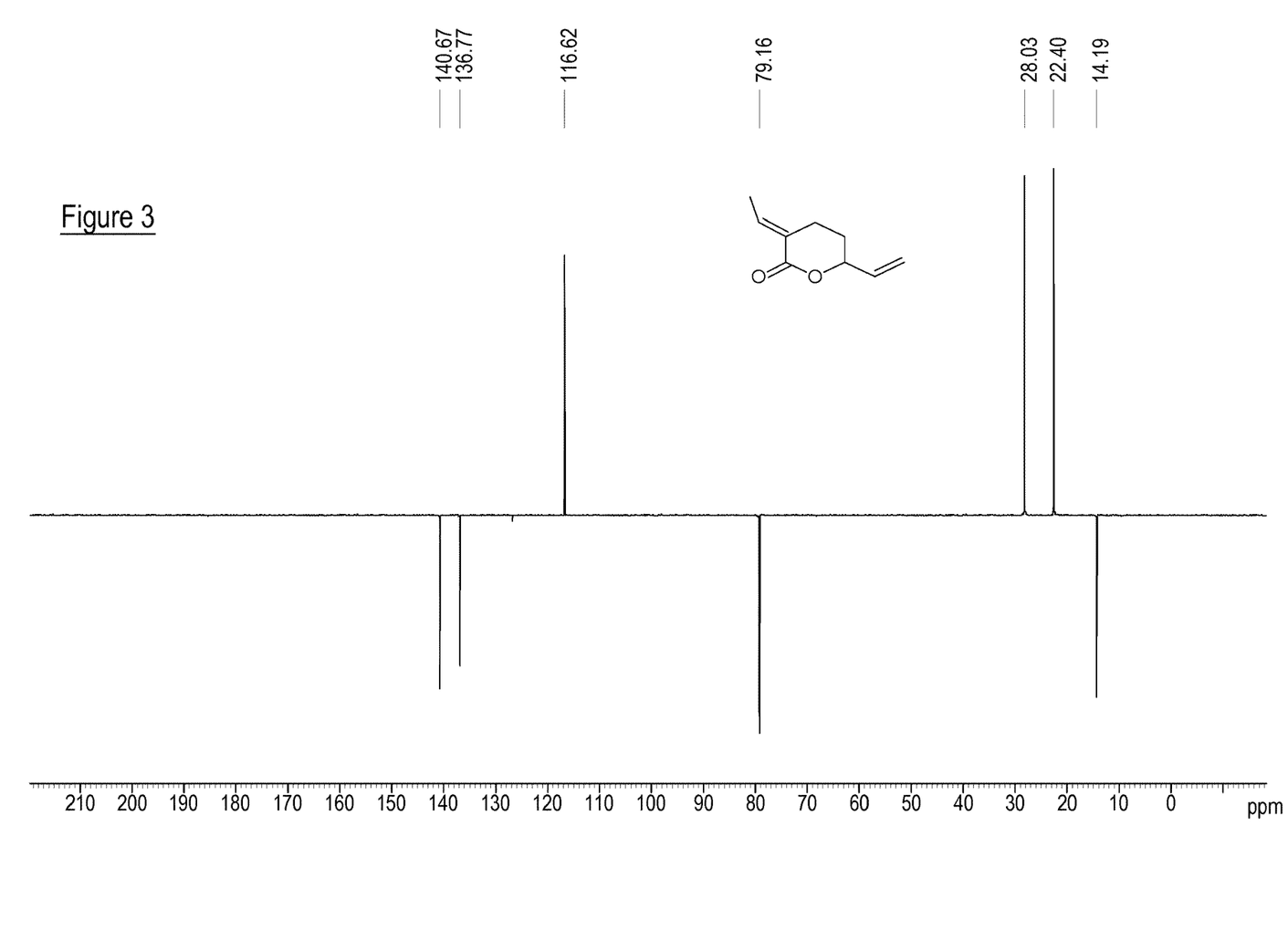
FIG. 3 shows a $^{13}$C-Dept. NMR spectrum for δ-lactone (1) formed according to a method of the present invention.

Nuclear magnetic resonance (NMR) spectra ($^1$H, $^{13}$C, $^{13}$C-Dept.; FIGS. 1, 2 and 3) were recorded on Bruker ($^1$H: 300 MHz, $^{13}$C: 75 MHz, $^{13}$C Dept.: 75 MHz) recorded in a $CDCl_3$ solution recorded on a PerkinElmer FTIR 430 spectrometer. High-resolution mass spectra were recorded in our analytical department whereas GC yields were recorded on (GC: Agilent 7890A, Column. Agilent 19091J-43. 325° C.: 30 m*320 μm*0.25 μm) using method: 50°[8]-260°[8])-320 [8].

General Procedure for the synthesis of δ-lactone (1)
Pd-precatalyst (x mg, x mmol, 0.06 mol %) and Lx (x mg, x mmol, 0.18 mol %) were prepared in a Schlenk flask in MeCN (30) under argon (Ar) and then transferred to a 50 mL autoclave. The sealed autoclave was purged with Ar three times. 1,3-Butadiene (3.00 g, 55.5 mmol) was then charged in autoclave at −20° C. and then the autoclave was charged with $CO_2$ (3.50 g, 80 mmol). The autoclave was placed in aluminium block at 78-80° C. for 16 h. Upon completion of the desired reaction time, the autoclave was cooled to room temperature with ice-water bath. The remaining gas was released. The diglyme as an internal standard was added to the reaction mixture and then measured the GC yields. The rest crude product was purified by silica gel chromatography (2:10 ethyl acetate/heptane to get isolated light yellow oil. The yields of δ-lactone (1) as well as the amounts of Pd precursors and phosphine ligands were all calculated based on the basis of 1,3-butadiene.

$^1$H NMR (300 MHz, $CD_2Cl_3$) 1.2-1.71 (m, 1H), 1.73-1.76 (m, 3H), 2.34-2.47 (m, 1H), 2.56-2.61 (m, 1H), 4.69-4-76 (m, 1H), 5.19 (ddd, J=1.34, 1.34, 10.6 Hz, 1H), 5.30 (ddd, J=1.34, 1.34, 17.1 Hz, 1H), 5.82-592 (m, 1H), 6.95-7.04 (m, 1H); $^{13}$C NMR (75.4 MHz) 13.6, 21.8, 27.4, 78.5, 116.0, 126.2, 136.2, 140.1, 165.2; GC-MS: 152(7), 137(12), 124 (42), 109(32), 97(14), 91(17), 81(34), 79(22), 67(88), 50(13), 41(44), 39(100), 38(12); HRMS (ESI) calcd. For $[M+H]^+$ $C_9H_{12}O_2$: 153.09101 $[M+H]^+$; found: 153.0915.

The $^1$H NMR, $^{13}$C NMR and $^{13}$C-Dept. NMR for δ-lactone (1) are shown in the figures.

Alternative Phosphine Ligands

In non-limiting examples, δ-lactone (1) was produced from 1,3-butadiene and carbon dioxide in high yield and selectivity. The reactions took place in the presence of $Pd(acac)_2$ and used a number of alternative phosphine ligands (L1 through to L18; see Scheme 3).

Scheme 3. Screening of phosphine ligands for Palladium-catalyzed telomerization of 1,3-butadiene with $CO_2$; General Reaction conditon.

L6 (Y., 52%; Sel., 92%)
L6 (Y., 11%; Sel., 94%)  L7 (Y., 30%; Sel., 65%)

L8 (Y., 20%; Sel., 60%)   L9 (.Y, Traces)

L10 R = Ph (Y., Traces)
L11 R = Cy (Y., Traces)   L12 (Y., 10% Sel., 80%)

L13 (Y., 30%; Sel., 95%)

L14 (Y, Traces)   L15 (Y., Traces)

L16 (Y., 85%; Sel., 28%)   L17 (Y., 40%; Sel., 91%)

L18 (Y., 20%; Sel., 81%)

a; (x mmol; x mmol shows that the processes are scalable to higher mass ratios whilst keeping the mole ratios the same) of 1,3-butadiene, $CO_2$, Pd(acac)$_2$ (0.06 mol %), L (0.18 mol %), MeCN. b; Yields of mixture of 1-4 were determined by GC with internal standard diglyme. *Reaction conducted at 90° C. ** Reaction with 10 bar of $N_2$ in addition to $CO_2$. Y., = (Product 1-4, Sel., Selectivity of product 1)

In this example, applying phosphine ligands L9-L11 and L14-L15 in the presence of Pd(acac)$_2$ in the reaction of 1,3-butadiene with carbon dioxide afforded traces of δ-lactone (1). Despite this, these ligands are expected to provide higher yields under different reaction conditions.

L1-L3, L7, L8, L12, L13 and L17 provided δ-lactone (1) in relatively high yield and selectivity. L16 afforded 85% yield with 28% selectivity towards the desired product δ-lactone (1).

L4 and L5 provided yields of 62%, 70% with 90% and 80% of selectivity for the desired product δ-lactone (1) respectively. The ligand L4 (TOMPP=tris-(o-methoxyphenyl)phosphine) was found to be a preferable ligand to afford the desired product δ-lactone (1) in good yield and with high selectivity.

Alternative Pd Catalysts

The present inventors tested alternative Pd catalysts. L4 was chosen as the phosphine ligand. As presented in Table 1, Pd catalyst precursors influenced the formation of δ-lactone (1). Pd(dba)$_2$ yielded 73% with 92% selectivity of product δ-lactone (1) with 608 TON (Table 1, entry 3) whereas Pd$_2$(dba)$_3$ afforded the 74% yield with 91% selectivity respectively with TON 751 (Table 1, entry 5). Pd$_2$(dba)$_3$ also afforded 58% with 91% selectivity after 15 h whereas 60% yields, 95% selectivity of δ-lactone 1 with 1500 TON was obtained when 0.02 mol % Pd$_2$(dba)$_3$/L4 (TOMPP 0.06 mol %) was applied for 20 h (Table 1, entries 6, 7).

TABLE 1

Effect of different Pd precursors on telomerization of 1,3-butadiene with carbon dioxide

| Entry | Pre-catalyst | Yield(1 + 2A + 3 + 4) (%)[b] | Selectivity 1 (%)[b] | TON |
|---|---|---|---|---|
| 1 | Pd(OAc)$_2$ | 31 | 55 | 250 |
| 2 | PdCl$_2$(MeCN)$_2$ | 70 | 50 | 586 |
| 3 | Pd(dba)$_2$ | 73 | 92 | 608 |
| 4 | [PdCl(allyl)]$_2$ | 46 | 82 | 363 |
| 5[c] | Pd$_2$(dba)$_3$ | 74 | 91 | 751 |

TABLE 1-continued

| | | | | |
|---|---|---|---|---|
| 6[d] | Pd$_2$(dba)$_3$ | 58 | 91 | 586 |
| 7[e] | Pd$_2$(dba)$_3$ | 60 | 95 | 1500 |

General Reaction conditions.

[a](x mmol) of 1,3-butadiene, CO$_2$, Pd-precatalyst (0.06 mol %), L4 (0.18 mol %).

[b]Yields and selectivities, were determined by GC with internal standard diglyme.

[c][Pd] 0.05 mol %, L4: 0.15 mol %.

[d]15 h.

[e][Pd] 0.02 mol %, L: 0.06 mol %

Palladium Catalyst/Ligand Combinations

In other examples, reactions were performed applying Pd precursors with alternative ligands, L5-L7. These studies found that L6 in combination with Pd(dba)$_2$ effects telomerization 1,3-Butadiene and CO$_2$ in 71% yield with more than 90% selectivity and 593 TON (Table 2, entry 1).

TABLE 2

Parameters for telomerization of 1,3-butadiene with carbon dioxide

| Entry | Pre-catalyst | Ligand | Yields (1-4)[b]/ Sel. (1) (%) | TON |
|---|---|---|---|---|
| 1 | Pd(dba)$_2$ | L 6 | 71/>90 | 593 |
| 2[c] | Pd(dba)$_2$ | L 7 | 64/20 | 640/160* |
| 3 | Pd(dba)$_2$ | L 5 | 74/70 | 616 |
| 4[c] | Pd$_2$(dba)$_3$ | L 5 | 60/46 | 602/261* |

General Reaction conditions.

[a](x mmol) of 1,3-butadiene, CO$_2$, Pd-precatalyst (0.06 mol %), L5, L6, L7 (0.18 mol %).

[b]Yields Yields and selectivities were determined by GC with internal standard diglyme.

[c][Pd] 0.05 mol %, L5: 0.15 mol %.

*TON of desired product 1

Alternative Diene Reactant (1,2-butadiene)

The present inventors also performed the Pd/TOMPP catalyzed telomerization of 1,2-butadiene with carbon dioxide and have found up to 10%, 22% yields with 50% and 60% selectivities of δ-lactone 1 (Scheme 4).

Scheme 4. Ligands screening for Palladium-catalyzed telomerization of 1,2-butadiene with carbon dioxide L3 (Y., 10%; Sel., 50% 1
L4 (Y., 22%; Sel., 60% 1

It is anticipated that Pd/phosphine ligand catalyzed telomerization, in the presence of carbon dioxide, is applicable to molecules of the general formulae:

Conclusion

The present inventors have demonstrated different palladium catalyst systems for telomerization of different compounds, e.g. compounds (II), (III) and (IV) above. In particular, the reaction of 1,3-butadiene with carbon dioxide for the synthesis of δ-lactone (1) has been shown in high yield, with excellent selectivity and superior TON under mild conditions.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

In closing, it is to be understood that the embodiments of the disclosure disclosed herein are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

REFERENCES

For the avoidance of doubt, protection may be sought for the features disclosed in any one or more of the referenced documents in combination with this disclosure.

Each of the following references is incorporated herein by reference in its entirety:
1. L. Wu, Q. Liu, I. Fleischer, R. Jackstell and M. Beller, Nature communications, 2014, 5.
2. W. McDonough, M. Braungart, P. T. Anastas and J. B. Zimmerman, Environmental science & technology, 2003, 37, 434A-441A.
3. A. Behr, A. J. Vorholt, K. A. Ostrowski and T. Seidensticker, Green Chemistry, 2014, 16, 982-1006.
4. Q. Liu, L. Wu, R. Jackstell and M. Beller, Nature communications, 2015, 6.
5. R. Nakano, S. Ito and K. Nozaki, Nature chemistry, 2014, 6, 325-331.
6. Y. Tsuji and T. Fujihara, Chemical communications, 2012, 48, 9956-9964.
7. M. Aresta and A. Dibenedetto, Dalton Transactions, 2007, 2975-2992.
8. M. Mikkelsen, M. Jørgensen and F. C. Krebs, Energy & Environmental Science, 2010, 3, 43-81.
9. C. Maeda, Y. Miyazaki and T. Ema, Catalysis Science & Technology, 2014, 4, 1482-1497.
10. D. Fromm and D. LUTZOW, CHEMIE IN UNSERER ZEIT, 1979, 13, 78-81.
11. T. Sakakura and K. Kohno, Chemical Communications, 2009, 1312-1330.
12. J. V. Ochoa, C. Bandinelli, O. Vozniuk, A. Chieregato, A. Malmusi, C. Recchi and F. Cavani, Green Chemistry, 2016.
13. J. H. Clements, Industrial & engineering chemistry research, 2003, 42, 663-674.
14. M. Aresta, A. Dibenedetto and A. Angelini, Chemical Reviews, 2014, 114, 1709-1742.
15. A. R. Elsagir, F. Gaßner, H. Görls and E. Dinjus, Journal of Organometallic Chemistry, 2000, 597, 139-145.
16. S. Inoue, ( ) Chem. Econ, Eng. Rev, 1975, 7, 31.
17. Y. Inoue, T. Hibi, M. Satake and H. Hashimoto, Journal of the Chemical Society, Chemical Communications, 1979, 982-982.
18. A. Musco, C. Perego and V. Tartiari, Inorganica Chimica Acta, 1978, 28, L147-L148.
19. A. Behr, K.-D. Juszak and W. Keim, Synthesis, 1983, 1983, 574-574.
20. V. Haack, E. Dinjus and S. Pitter, Die Angewandte Makromolekulare Chemie, 1998, 257, 19-22.
21. A. Behr and V. A. Brehme, Journal of Molecular Catalysis A: Chemical, 2002, 187, 69-80.
22. A. Behr and V. A. Brehme, Advanced Synthesis & Catalysis, 2002, 344, 525-532.
23. A. Behr, M. Urschey and V. A. Brehme, Green Chemistry, 2003, 5, 198-204.
24. A. Behr, G. Henze, L. Johnen and S. Reyer, Journal of Molecular Catalysis A: Chemical, 2008, 287, 95-101.
25. R. Martin and A. W. Kleij, ChemSusChem, 2011, 4, 1259-1263.
26. A. Behr and G. Henze, Green Chemistry, 2011, 13, 25-39.
27. C.-F. Huo, R. Jackstell, M. Beller and H. Jiao, Journal of Molecular Modeling, 2009, 16, 431-436.
28. R. Jackstell, A. Grotevendt, M. G. Andreu and M. Beller, Organic Process Research & Development, 2009, 13, 349-353.
29. N. D. Clement, L. Routaboul, A. Grotevendt, R. Jackstell and M. Beller, Chemistry—A European Journal, 2008, 14, 7408-7420.
30. A. Grotevendt, M. Bartolome, D. J. Nielsen, A. Spannenberg, R. Jackstell, K. J. Cavell, L. A. Oro and M. Beller, Tetrahedron Letters, 2007, 48, 9203-9207.

31. R. Jackstell, S. Harkal, H. Jiao, A. Spannenberg, C. Borgmann, D. Röttger, F. Nierlich, M. Elliot, S. Niven, K. Cavell, O. Navarro, M. S. Viciu, S. P. Nolan and M. Beller, Chemistry—A European Journal, 2004, 10, 3891-3900.
32. Y. Dai, X. Feng, B. Wang, R. He and M. Bao, Journal of Organometallic Chemistry, 2012, 696, 4309-4314.
33. Y. Dai, X. Feng, B. Wang, R. He and M. Bao, Journal of Organometallic Chemistry, 2012, 696, 4309-4314.
34. A. Behr, R. He, K.-D. Juszak, C. Krüger and Y.-H. Tsay, Chemische Berichte, 1986, 119, 991-1015.
35. A. Behr and M. Becker, Dalton Transactions, 2006, 4607-4613.

The invention claimed is:

1. A method of forming a compound of formula (I):

the method comprising the steps of:
(i) providing a compound of the formula (II), (III) or (IV):

wherein,
$R_1$ is H, unsubstituted alkyl, substituted alkyl, unsubstituted phenyl or substituted phenyl;
$R_2$ is H, unsubstituted alkyl, substituted alkyl, unsubstituted phenyl or substituted phenyl;
$R_3$ is H;
$R_4$ is H, unsubstituted alkyl, substituted alkyl, unsubstituted phenyl or substituted phenyl; and,
(ii) reacting the compound of formula (II), (III) or (IV) with $CO_2$ in the presence of a source of Pd(0) and a phosphine ligand to form the compound of formula (I), wherein the phosphine ligand is any one of:

$P(2\text{-OMe-Ph})_3$, $P(2\text{-furyl})_3$, and wherein Ph is —C$_6$H$_5$, Cy is —C$_6$H$_{11}$, Me is —CH$_3$ and Ad is adamantyl.

2. The method of claim 1, wherein the term substituted refers to the particular moiety substituted with 1, 2, 3, 4, 5, 6, 7, 8, 9, 10, 11, 12, 13, 14, 15, 16, 17, 18, 19 or 20 substituents selected from the group consisting of H, alkyl, aryl, alkenyl, alkynyl, arylalkyl, alkoxy, aryloxy, arylalkoxy, alkoxyalkylaryl, alkylamino, arylamino, 2-OMe-Ph, phenyl, 2-furyl, NH$_2$, OH, CN, NO$_2$, OCF$_3$, CF$_3$, Br, Cl, F, 1-amidino, 2-amidino, alkylcarbonyl, morpholino, piperidinyl, dioxanyl, pyranyl, heteroaryl, furanyl, thiophenyl, tetrazolo, thiazole, isothiazolo, imidazolo, thiadiazole, thiadiazole S-oxide, thiadiazole S,S-dioxide, pyrazolo, oxazole, isoxazole, pyridinyl, pyrimidinyl, quinoline, isoquinoline, SR''', SOR''', SO$_2$R''', CO$_2$R''', COR''', CONR'''R''', CSNR'''R''' and SO$_n$NR'''R''', wherein R''' is alkyl or substituted alkyl.

3. The method of claim 1, wherein the source of Pd(0) is selected from the group consisting of Pd(acac)$_2$, Pd(OAc)$_2$, PdCl$_2$(MeCN)$_2$, Pd(dba)$_2$, [PdCl(allyl)]$_2$, Pd$_2$(dba)$_3$, and a Pd(II) complex that can be reduced in situ to produce Pd(0) species.

4. The method of claim 1, wherein R$_1$, R$_2$, R$_3$ and R$_4$ are each H.

5. The method of claim 1, wherein the step of providing a compound of formula (I) includes providing 1,3-butadiene

.

6. The method of claim 1, wherein the method is a method of forming δ-lactone, namely,

.

7. The method of claim 1, wherein the step of reacting the compound of formula (II), (III) or (IV) with CO$_2$ in the presence of the source of Pd(0) and the phosphine ligand to form the compound of formula (I) takes place in a solvent.

8. The method of claim 7, wherein the solvent is MeCN, propylene carbonate or ethylene carbonate.

9. The method of claim 1, wherein the step of reacting the compound of formula (II), (III) or (IV) with CO$_2$ in the presence of the source of Pd(0) and the phosphine ligand to form the compound of formula (I) utilises CO$_2$ as a reactant in gaseous form.

10. The method of claim 1, wherein the method is a method of forming δ-lactone, namely,

, the method comprising the steps of:
(i) providing 1,3-butadiene

;

and,
(ii) reacting 1,3-butadiene with CO$_2$ in the presence of the source of Pd(0) and the phosphine ligand to form δ-lactone.

11. The method of claim 1, wherein the source of Pd(0) is Pd(acac)$_2$.

12. The method of claim 1, wherein the phosphine ligand is P(2-OMe-Ph)$_3$ (TOMP; tris(2-methoxyphenyl)phosphine).

* * * * *